(12) United States Patent
Varanasi et al.

(10) Patent No.: US 8,227,400 B2
(45) Date of Patent: *Jul. 24, 2012

(54) AIR TREATMENT DEVICE WITH CONTROLLED PORE SIZE SUBSTRATE

(75) Inventors: Padma Prabodh Varanasi, Racine, WI (US); Joel E. Adair, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 26 days.

This patent is subject to a terminal disclaimer.

(21) Appl. No.: 12/882,555

(22) Filed: Sep. 15, 2010

(65) Prior Publication Data

US 2011/0220731 A1 Sep. 15, 2011

Related U.S. Application Data

(62) Division of application No. 11/348,989, filed on Feb. 7, 2006, now Pat. No. 7,820,188.

(51) Int. Cl.
*A61K 7/46* (2006.01)
(52) U.S. Cl. .................. 512/4; 424/400; 428/304.4
(58) Field of Classification Search .............. None
See application file for complete search history.

(56) References Cited

U.S. PATENT DOCUMENTS

| 3,806,323 A | 4/1974 | Thompson |
| 5,246,919 A | 9/1993 | King |
| 6,909,840 B2 * | 6/2005 | Harwig et al. ............... 392/405 |

FOREIGN PATENT DOCUMENTS

| GB | 789769 | 1/1958 |
| WO | WO 96/33605 | 1/1958 |
| WO | WO 97/10009 | 3/1997 |

OTHER PUBLICATIONS

International Search Report and Written Opinion dated Jul. 23, 2007, PCT/US2007/002834.

* cited by examiner

*Primary Examiner* — Neil Levy

(57) ABSTRACT

Disclosed are substrates suited for dispensing air treatment chemicals upon being heated. Granular particles, preferably sand with a phenolic binder, are adhered together to form a substrate body having a network of pores. A volatile air treatment chemical is disposed in the pores. The particle size and pores are such that the smaller particles of the substrate are grouped at one end, preferably an end adjacent to a projecting nose. This structure tends to wick the volatile air treatment chemical towards the nose, and heating that area can lead to efficient, and rechargeable, dispensing. Methods for using such substrates, and methods for forming such substrates, are disclosed.

7 Claims, 4 Drawing Sheets

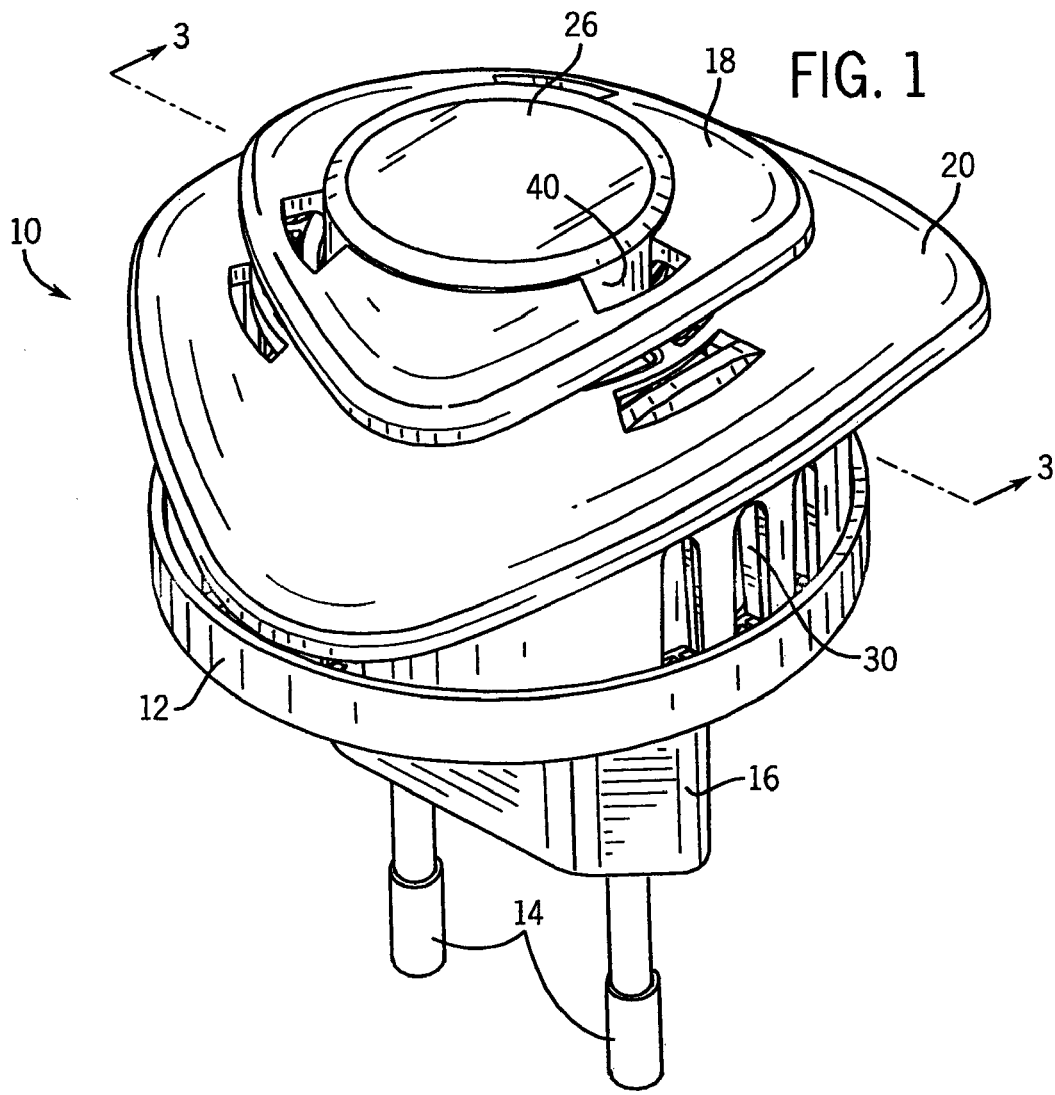
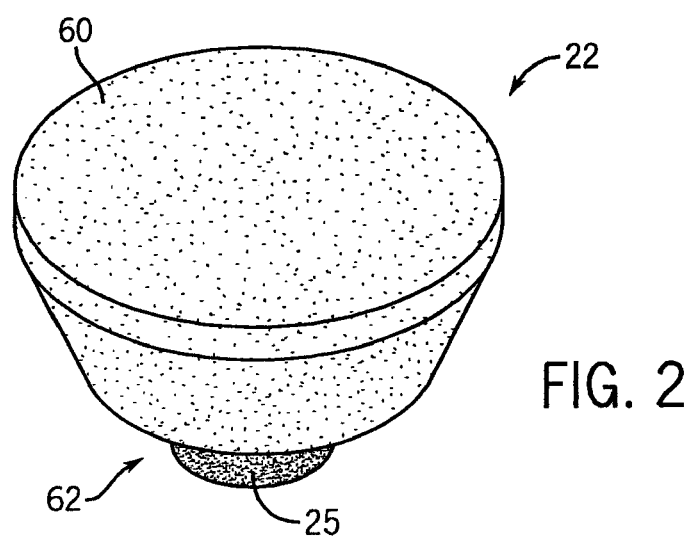

FIG. 7
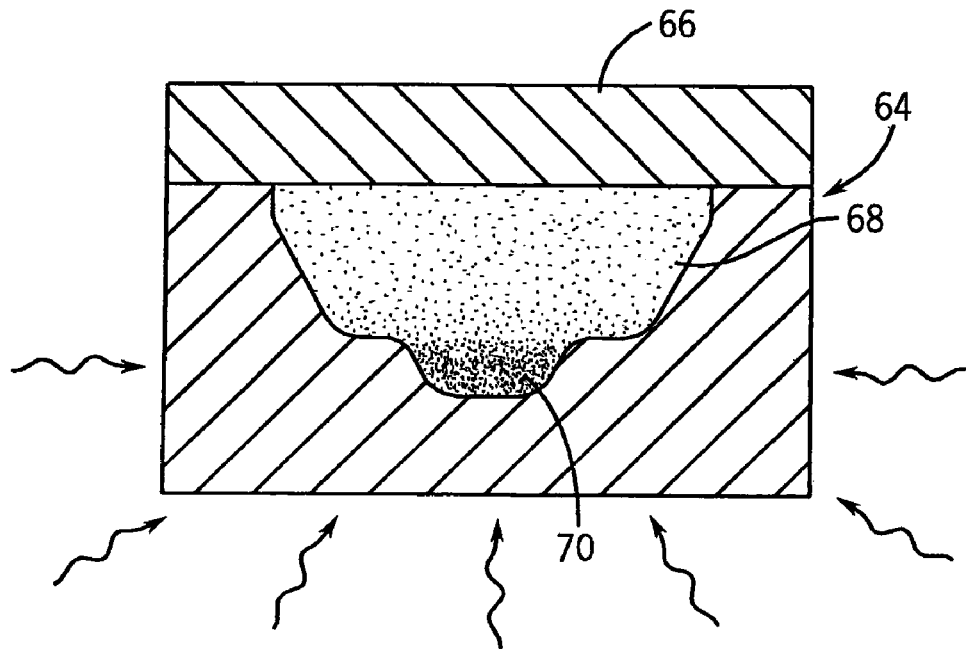
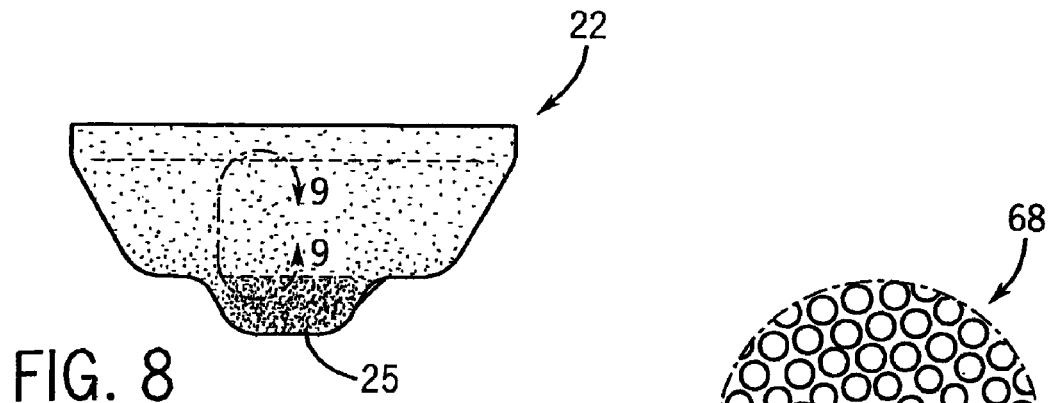
FIG. 8
FIG. 9
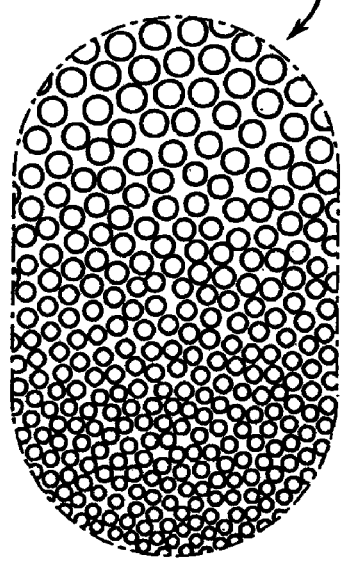

AIR TREATMENT DEVICE WITH CONTROLLED PORE SIZE SUBSTRATE

CROSS-REFERENCE TO RELATED APPLICATIONS

This application is a division of, and claims priority based on U.S. Ser. No. 11/348,989, filed Feb. 7, 2006.

STATEMENT REGARDING FEDERALLY SPONSORED RESEARCH/DEVELOPMENT

Not applicable

BACKGROUND OF THE INVENTION

The present invention relates to devices that dispense a volatile air treatment chemical by heating a substrate that is impregnated with, or coated with, the chemical. More particularly it relates to methods for constructing the substrate to create an array of pore size distribution therein, substrates produced thereby, and such substrates further formed with a rechargeable start-up projection.

Substrates (particularly porous substrates) have previously been used as carriers for air treatment chemicals such as insect control agents (insecticides, insect repellents, insect growth regulators, attractants, synergists, etc.), fragrances and deodorizers. See e.g. U.S. Pat. No. 6,551,560. The disclosure of this patent, and of all other patents referred to herein are incorporated by reference as if fully set forth herein.

Upon heating of the substrate a volatile air treatment chemical is caused to be dispensed from the substrate. The heating source is typically an electrical heater, but may instead be a flame in some cases.

A variety of air treating functions can be achieved with such devices. For example, a porous substrate impregnated with volatile insecticide can be used to inhibit mosquito biting in a confined bedroom. Alternatively, a deodorizing or other odor control material can be dispensed to overcome malodors, or to simply provide a desired fragrance.

One problem with such devices is that the substrate usually rests against or near a heater. The heater heats the substrate, causing the volatized air treatment chemical to be driven off the substrate in a direction away from (essentially perpendicular to) a heater surface. This can create some inefficiencies. For example, the portion of the substrate adjacent the heater can act as an insulator for the portion of the substrate which is releasing the active, making control of the dispensing more difficult.

Another problem with such devices is that it may take a while after usage begins to adequately treat the air in a defined environment adjacent the device. For example, when someone is about to go to bed they may activate the device in a bedroom. It is undesirable for them to have to wait a long period before feeling secure about insect protection in the room.

In connection with burnable mosquito coils, U.S. Pat. No. 5,948,425 disclosed in an enlarged outer end of the coil that would initially burn to create a burst of insecticide, before the rate of burning slowed down to a steady state. In connection with a non-burnable substrate, U.S. Pat. No. 6,551,560 disclosed that a central region could be provided having the ability to provide a quick burst of active, followed by the surrounding area releasing active at a slower constant rate. While these patents therefore addressed the need for quickly treating a room at the beginning of operation, they did not address a way to have the same device provide such a burst on multiple days.

In U.S. Pat. No. 4,286,754 and U.S. patent application publication 2004/0151747 it was discussed that a variety of wicks could be formed from sand (and certain other particulate material) mixed with a binder. The wicks could draw active from a reservoir to an upper portion of the wick, and the upper portion of the wick could be positioned adjacent to (usually through) a heater unit to volatize the active. For example, in U.S. patent application publication 2004/0151747 there is a discussion of forming the wick of silica sand particles bound with a novolac resin. The volatile material was described as optionally being an insecticide dissolved in a hydrocarbon solvent and/or a fragrance.

However, these wicks were not provided with a means of creating a quick start-up burst, much less a rechargeable start-up burst. Further, they required the use of a reservoir to continuously resupply the wick.

In unrelated work U.S. patent application publication 2004/0140114 disclosed that tapering pores in a housing can wick liquid away from a battery.

In any event, there is a need for producing porous substrates which efficiently dispense air treatment chemicals as well as have rechargeable start-up burst characteristics.

BRIEF SUMMARY OF THE INVENTION

In one aspect the invention provides a method for dispensing a volatile material from a substrate. One obtains a porous substrate having a projecting nose, the substrate being impregnated with a volatile air treatment chemical, heats the substrate such that heat is applied to at least an end of the nose to cause a first burst of volatile air treatment chemical to be dispensed from the substrate, allows the nose of the substrate to cool and permitting additional volatile air treatment chemical to be drawn from the substrate to the nose, and re-heats the substrate such that heat is applied to at least an end of the nose to cause a second burst of volatile air treatment chemical to be dispensed from the substrate. The porous substrate comprises sand and a binder.

In preferred forms of this method the substrate has a first end defined by the nose and a second opposed end, and an average size of the sand in the nose is less than an average size of the sand adjacent the second end, and the porous substrate further comprises a fragrance.

In another aspect the invention provides a substrate that can actively dispense a volatile air treatment chemical upon being heated. The substrate is formed from granular sand particles adhered together to form a body having a network of pores, and volatile air treatment chemical is disposed in the pores.

The substrate has a first end and a second opposed end, and an average size of the granular particles adjacent the first end is sufficiently less than an average size of the granular particles adjacent the second end such that the first end tends to wick air treatment chemical towards the first end as air treatment chemical is dispensed from pores of first end. As a result the substrate is capable of delivering a first burst of the volatile air treatment chemical from the first end when the substrate is heated adjacent the first end, and if thereafter the substrate is allowed to cool it is capable of delivering a second burst of the volatile air treatment chemical from the first end when the substrate is thereafter heated for a second time adjacent the first end. The second burst has at least in part volatile air treatment chemical that has been wicked towards the first end from elsewhere in the substrate, and the granular particles comprise sand and a binder such as a phenolic resin.

In yet another aspect the invention provides a method for forming a substrate that can actively dispense a volatile air treatment chemical upon being heated. One places sand particles in a mold, shakes the mold to cause smaller sand particles to move downward relative to larger sand particles in the mold, and thereafter forms the substrate in the mold. As a result, the average particle size of the substrate at the bottom of the substrate in the mold will be less than the average particle size of the substrate at the top of the substrate in the mold.

The sand can be impregnated after the shaking step and before the forming step. Alternatively, it can be impregnated by exposing the already-formed substrate to the impregnation fluid.

It should be appreciated that the substrates of the present invention are inexpensive to produce, use heat extremely efficiently, and are capable of multiple initiation bursts. The foregoing and other advantages of the present invention will be apparent from the following description. In the description that follows reference is made to the accompanying drawings which form a part thereof, and in which there is shown by way of illustration, and not limitation, expected preferred embodiments of the invention. Such embodiments do not necessarily represent the full scope of the invention, and reference should therefore be made to the claims herein for interpreting the scope of the invention.

BRIEF DESCRIPTION OF THE DRAWINGS

FIG. 1 is a lower frontal perspective view of an air treatment device suitable to use a preferred substrate of the present invention;

FIG. 2 is a frontal perspective view of a preferred substrate of the present invention;

FIG. 7 is a view similar to FIG. 6, but with heat being applied to the mold;

FIG. 8 is a view of the substrate formed in the FIG. 7 mold, after it has been removed from the mold; and FIG. 9 is a detailed view of the region designated 9-9 in FIG. 8.

DETAILED DESCRIPTION OF THE PREFERRED EMBODIMENTS

Figure 3:
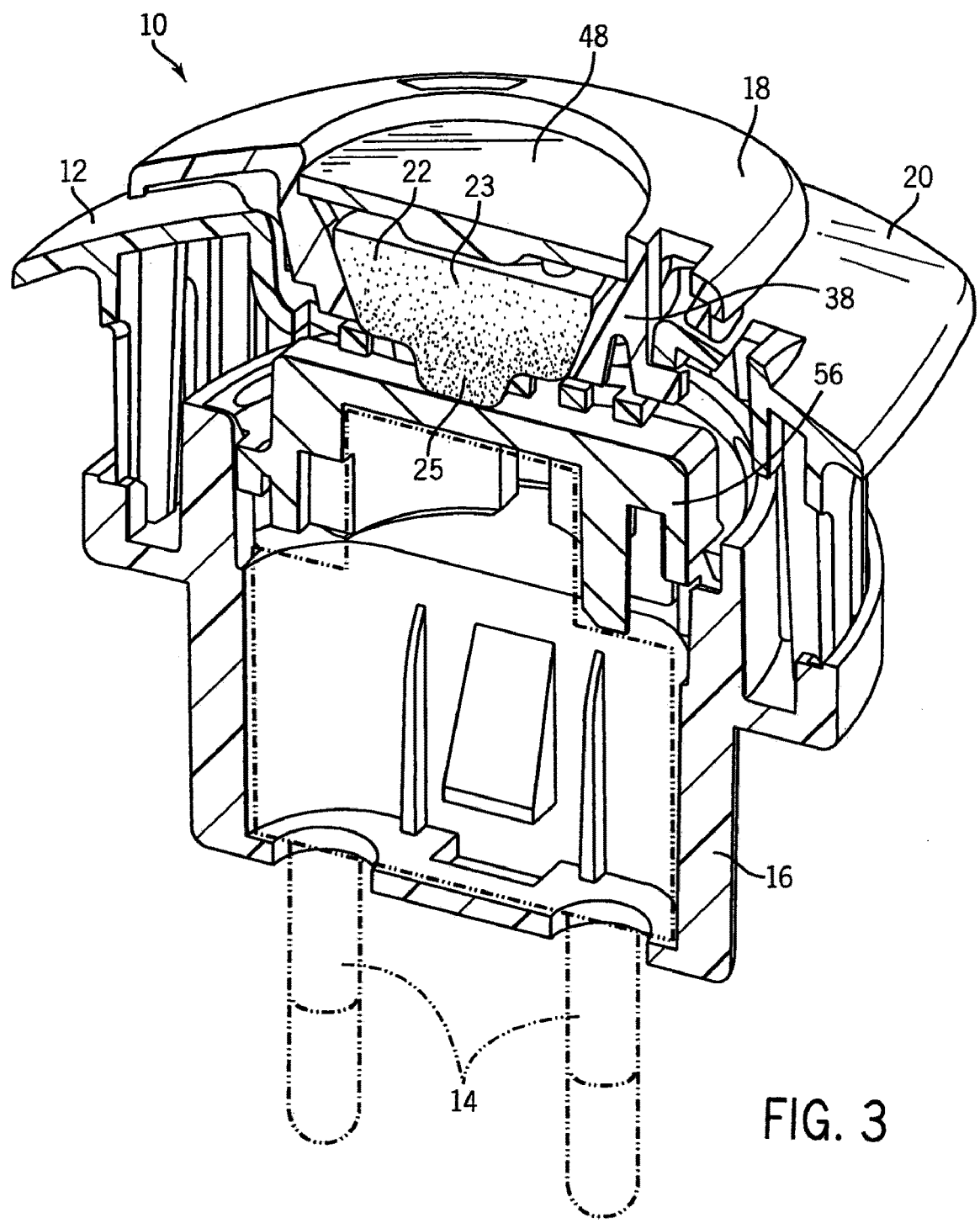
FIG. 3 is a sectional view of the FIG. 1 structure taken along line 3-3 of FIG. 1, albeit with an indicator unit 26 removed.
Figure 4:
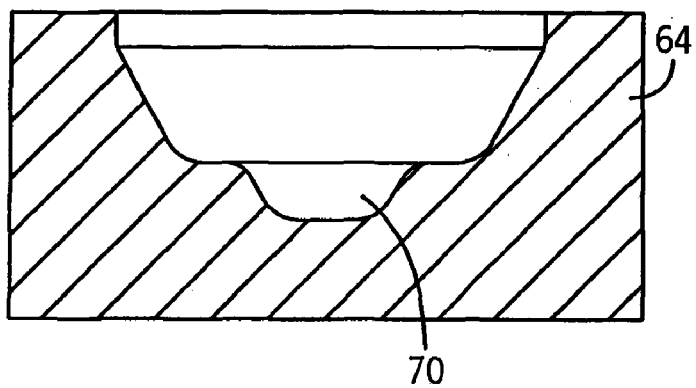
FIG. 4 is a sectional view of a mold used to prepare the substrate of FIG. 2.
Figure 5:
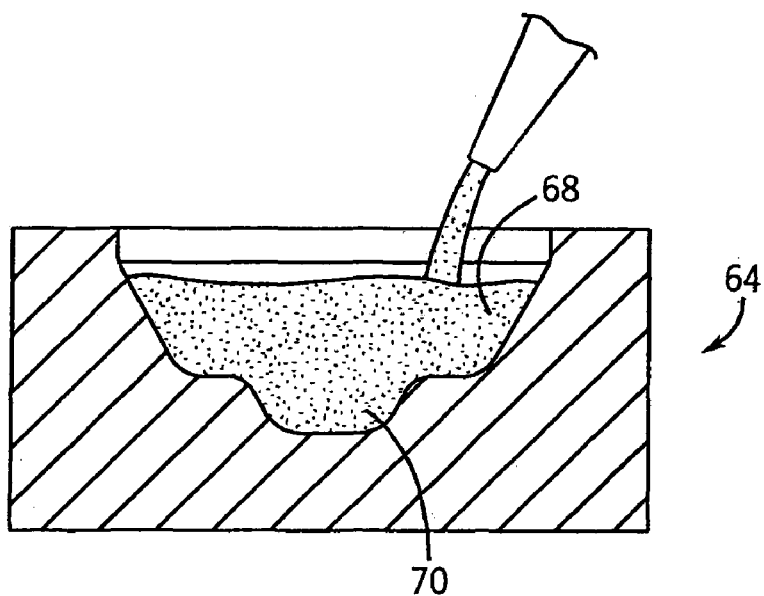
FIG. 5 is a view similar to FIG. 4, but with the mold shown partially filled.
Figure 6:
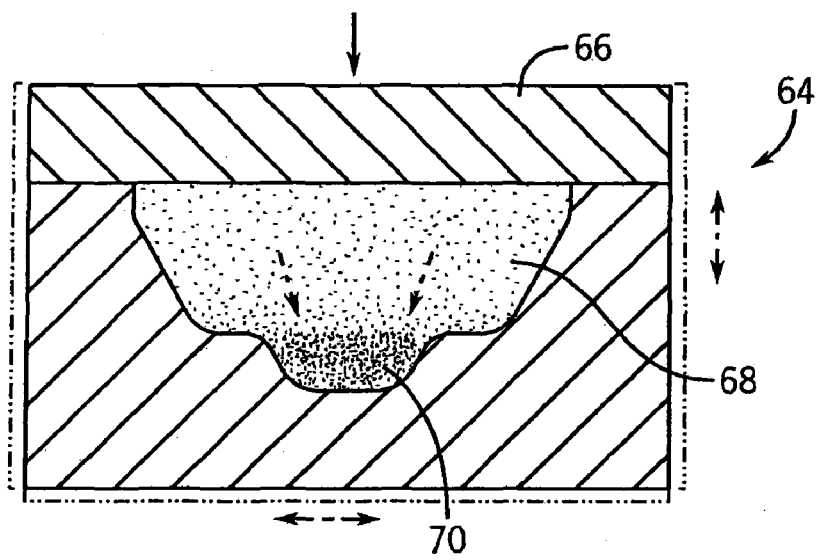
FIG. 6 is a view similar to FIG. 5, but with the mold shown filled, after it has been shaken, and after a cover/lid has been placed over the mold cavity.

Referring first to FIG. 1, air treatment device 10 has a housing 12 with electrical prongs 14 at a rear end 16 and a removable cartridge unit 18 at an opposing forward end 20.

The cartridge unit 18 preferably has a substrate 22 mounted to project through its rearward end and a separately installable indicator unit 26 mounted to project out from its forward end. There is a substantially circular cavity 38 (see FIG. 3) in the rearward center of the unit 18 which tapers rearwardly to hold the substrate 22.

The indicator unit 26 is removable from the cartridge unit 18. The indicator unit 26 preferably houses a separate indicator chemical, which may indicate to a user the amount of air treatment chemical remaining in the substrate 22. A removable indicator unit 26 allows the indicator unit 26 and/or the substrate 22 to be separately replaced. However, the indicator chemical may be directly housed in a well of the cartridge unit 18.

The device 10 is most preferably plugged into an electric socket on a vertical wall. Hence, the directional terms in this patent are used with that type of installation in mind. However, appropriate electric sockets on horizontal or other surfaces may also be used to provide power. Thus, the terms such as "front", "rear", "upper", "lower", and "side" should be interpreted in an analogous manner when the devices are used for that type of installation.

The prongs 14 shown in the figures are merely for purposes of example. Cylindrical prongs of this type are suitable for linking to electric power in some countries. However, in other countries blade prongs, or mixtures of blades, cylinders and other shaped prong elements will be used to supply the linkage to the available power (as is well recognized in the art).

The housing 12 has a series of elongated vents 30 on the upper and lower sides of the housing 12. The vents 30 allow in air from the environment and permit it to pass along with the air treatment chemical dispensed from the substrate 22 through the vents 30 on the upward side of the housing 12. Nose 25 of the substrate 22 is preferably positioned closely adjacent the heating element 56 with room around the nose 25 for air to pass completely around its periphery.

As is evident from FIGS. 2 and 3, the preferred cartridge unit 18 has a substrate 22 having a forward frustum shaped section 23 and a rearward projecting nose 25. The particular shape of the substrate 22 is not critical insofar as the broadest aspects of the invention are concerned. However, the projecting nose 25 has certain advantages for quick start-up in some preferred embodiments.

The substrate 22 is preferably impregnated with a volatile air treatment chemical capable of being dispensed from the substrate 22 when the substrate 22 is heated. However, as an alternative to being completely impregnated with the air treatment chemical, the substrate 22 may instead be only partially impregnated. The extent of dispensing of the air treatment chemical can be indicated by a visible cue whose appearance results from the dispensing of an indicator chemical 28 associated with the indicator unit 26.

Referring specifically to FIG. 2, the substrate 22 has a first end 62 and a second end 60 opposed to the first end, and the average size of the granular particles adjacent the first end 62 is less than the average size of the granular particles adjacent the second end 60. The substrate 22 thus is preferably configured such that the first end 62 tends to wick air treatment chemical towards itself as air treatment chemical is dispensed from the second end 60.

The housing 12 of the overall device 10 preferably encloses a heating element 56 such that the heating element 56 is positioned proximal to a rearward end of the cartridge unit 18. The heating element 56 is preferably activated by inserting the electrical prongs 14 into an outlet (not shown).

Heat from the heating element 56 may also be permitted to pass against other surfaces of the cartridge unit 18 through a series of openings. Note however a separator panel 48 (as shown in FIG. 3) which provides some insulation to the indicator unit 26.

The substrate 22 is preferably positioned in front of the heating element 56 with the nose 25 of the substrate 22 (containing the highest density and smallest pore size) closest to the heating element 56.

In use, heat is applied to at least an end and side walls of the nose of the substrate. This causes a first burst of the volatile air treatment chemical to be dispensed from the substrate.

Upon dispensing the first burst of air treatment chemical and typically after a continuing period of use, the nose of the substrate is preferably allowed to cool, thus permitting additional volatile air treatment chemical to be drawn from the substrate to the nose 25. Then, the substrate is re-heated such that heat is applied to at least a rearward end and side walls of the nose, causing a second burst of volatile air treatment chemical to be dispensed from the substrate.

Referring next to FIGS. 4-9, a method for forming the substrate 22 of the present invention is schematically depicted. A mold 64 of the substrate 22, having a projecting nose 70, is filled with the substrate material, preferably a sand/resin mix. The mold 64 is then covered with a lid 66 and shaken. By shaking the mold 64, the sand particles 68 having a smaller size are shifted downward, towards the nose 70 of the mold 64. In this manner, a substrate 22 having smaller particle size at the bottom end and larger particle size at the top end of the substrate 22 is formed.

Examples of a suitable substrate 22 include but are not limited to porous sand with a binder such as novolac resin, urethane resins or highly cross linked thermoplastics such as cross linked polyethylene. Particularly preferred sand substrates can be made in a fashion analogous to the sand wicks described in U.S. patent application publication 2005/0284952. Alternative substrates include other particulates such as metal, cellulose and ceramic particulates.

The air treatment chemical is preferably an insecticide, fragrance and/or disinfectant. In some cases more than one air treatment chemical may be used alone or in combination in the substrate 22.

When the air treatment chemical is an insecticide and/or insect repellent, organic phosphorous insecticides, lipidamide insecticides, natural repellents as citronella oil, natural pyrethrins and pyrethrum extract, and synthetic pyrethroids are preferred. Suitable synthetic pyrethroids are acrinathrin, allethrin as D-allethrin, Pynamin®, benfluthrin, bifenthrin, bioallethrin as Pynamin Forte®, S-bioallethrin, esbiothrin, esbiol, bisoresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, taufluvalinate, kadethrin, permethrin, phenothrin, prallethrin as Etoc®, resmethrin, tefluthrin, tetramethrin, tralomethrin, metofluthrin or transfluthrin. Other volatile insecticides, such as those described in U.S. Pat. No. 4,439,415, can also be employed.

In particularly preferred versions the volatile insecticide is selected from the group consisting of transfluthrin, metofluthrin, vapothrin, permethrin, prallethrin, tefluthrin and esbiothrin. Transfluthrin is the most preferred insecticide.

Possible solvents for carrying these air treatment chemicals include, but are not limited to, ISOPAR™C, ISOPAR™E, ISOPAR™L, heptane, methanol, acetone, ethanol, isopropyl alcohol, dodecene and tetraydrofuran. ISOPAR™C, ISOPAR™E and ISOPAR™L are hydrocarbon solvents of varying chain length and are available from Exxon Chemical Company.

Typically, volatile insect control agents will be carried in an organic solvent such as a hydrocarbon. One particularly desirable impregnation formulation for mosquito control is 50 wt. percent transfluthrin dissolved in ISOPAR C hydrocarbon. Alternatively, and often preferably, transfluthrin can first be warmed to liquefy it and then applied neat to a warmed substrate.

A wide variety of volatile fragrances may be used which may optionally also have insect control attributes. Alternatively, some fragrances may be selected that provide a deodorizing function (e.g. certain terpenes). For example, various natural and artificial perfumes may be used. Non-limiting examples of these perfumes include animal-based and plant-based natural perfumes, and artificial perfumes such as alcohols, phenols, aldehydes, ketones, terpenes, and esters When an volatile air treatment chemical is a disinfectant, preferred disinfectants include, but are not limited to, glycols, trimethylene and dipropylene. Organic acids compatible with the use of the substrate 22 and environment may also be used.

Regarding the amount of particles 68, either sand or otherwise, the mold 64 should be filled to capacity, thereby creating a substrate 22. The sand or other particulate should be shaken thoroughly in the mold (e.g. for ten or more seconds), although the exact time and degree of force required will depend on the type of particles 68 and the needs of the user.

The lid 66 can be present during the shaking. However, it is preferred that it be removed with the top of the sand smoothed, by dragging a blade across it, prior to starting the heating.

As one example, we formed a substrate of the FIG. 2 shape where the front wall had a diameter of 1.6 cm and the rear nose had a rear view maximum diameter of 0.5 cm. To do this, we placed 1.85 g of silica sand along with 0.07 g of novolac resin uniformly mixed therein, in a suitable shaped mold. We then shook the mold for 15 seconds, smoothed the top of the sand mix, and heated the mold for 10 minutes at 300.degree.C. We allowed the mold to cool and added 300 mg of transfluthrin by gently positioning it on the top surface of the sand. We removed the formed substrate, positioned it in a device like that of FIG. 3, and tested the operation of the device with an insect challenge.

The mold 64 used to form the substrate 22 of the present invention may be made from any suitable material, including but not limited to plastic, metal or wood molds. Hence, the mold itself is not critical.

While the preferred embodiment of the present invention has been described above, it should be appreciated that the invention could be used in a variety of other embodiments. For example, instead of adding the neat active or the impregnation fluid after the formation of the substrate, one could dose the active on the substrate in the mold prior to the formation of the substrate. One could also dip a formed substrate into a fluid bath containing 50% transfluthrin and 50% ISOPAR C.

Thus, the principles of the present invention can be applied in a wide variety of other ways apart from those specifically noted herein. Still other modifications may be made without departing from the spirit and scope of the invention. Thus, the claims (rather than just the preferred embodiment) should be reviewed in order to understand the full scope of the invention.

Industrial Applicability

The present invention provides improved substrates for use with air treatment devices, along with improved methods to make such substrates.

We claim:

1. A substrate that can actively dispense a volatile air treatment chemical upon being heated, the substrate comprising:
    granular sand particles adhered together to form a body having a network of pores; and
    volatile air treatment chemical disposed in the pores;
    wherein the substrate has a first end and a second opposed end; and wherein an average size of the granular particles adjacent the first end is sufficiently less than an average size of the granular particles adjacent the second end such that the first end tends to wick air treatment chemical towards the first end as air treatment chemical is dispensed from pores of first end;

whereby the substrate is capable of delivering a first burst of the volatile air treatment chemical from the first end when the substrate is heated adjacent the first end, and wherein if thereafter the substrate is allowed to cool it is capable of delivering a second burst of the volatile air treatment chemical from the first end when the substrate is thereafter heated for a second time adjacent the first end, even without refreshing the substrate from an external reservoir supply of the air treatment chemical between the first burst and second burst, the second burst comprising volatile air treatment chemical that has been wicked towards the first end from elsewhere in the substrate;

wherein the granular particles comprise sand and a binder.

2. The substrate of claim 1, wherein the air treatment chemical is a fragrance.

3. The substrate of claim 1, wherein the binder is a phenolic resin.

4. The substrate of claim 1, wherein the substrate has a first end defined by a nose and a second opposed end, and an average size of the sand in the nose is less than an average size of the sand adjacent the second end.

5. A method for dispensing a volatile material from a substrate, comprising:

obtaining a porous substrate having a projecting nose, the substrate being impregnated with a volatile air treatment chemical;

heating the substrate such that heat is applied to at least an end of the nose to cause a first burst of volatile air treatment chemical to be dispensed from the substrate;

allowing the nose of the substrate to cool and permitting additional volatile air treatment chemical to be drawn from the substrate to the nose; and re-heating the substrate such that heat is applied to at least an end of the nose to cause a second burst of volatile air treatment chemical to be dispensed from the substrate;

wherein the porous substrate comprises sand and a binder and the substrate is a claim 4 substrate.

6. The method of claim 5, wherein the substrate has a first end defined by the nose and a second opposed end, and an average size of the sand in the nose is less than an average size of the sand adjacent the second end.

7. The method of claim 5, wherein the porous substrate further comprises a fragrance.

* * * * *